(12) United States Patent
Hand et al.

(10) Patent No.: US 6,358,232 B1
(45) Date of Patent: *Mar. 19, 2002

(54) METHOD AND APPARATUS FOR REMOVING AND DISPOSING OF BODY FLUIDS

(75) Inventors: Joseph M. Hand, Sheboygan Falls; Barry G. Anderson, Sheboygan; Michael C. Hollen, Manitowoc; Mark A. Miller, Kiel, all of WI (US)

(73) Assignee: Bemis Manufacturing Company, Sheboygan Falls, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/239,842

(22) Filed: Jan. 29, 1999

Related U.S. Application Data

(63) Continuation-in-part of application No. 08/877,771, filed on Jun. 17, 1997, now Pat. No. 5,871,476, which is a division of application No. 08/582,358, filed on Jan. 5, 1996, now Pat. No. 5,688,255, which is a continuation-in-part of application No. 08/547,759, filed on Oct. 24, 1995, now Pat. No. 5,683,371, which is a continuation-in-part of application No. 08/365,695, filed on Dec. 29, 1994, now Pat. No. 5,620,428.

(51) Int. Cl.⁷ ................................................ A61M 1/00

(52) U.S. Cl. ...................... 604/319; 604/317; 604/322; 141/329; 141/330

(58) Field of Search ................................ 604/317–326, 604/411–414; 141/329, 330

(56) References Cited

U.S. PATENT DOCUMENTS

| 1,421,325 A | 6/1922 | Walker et al. |
| 1,693,885 A | 12/1928 | Butterworth |
| 1,827,085 A | 10/1931 | Huff |
| 2,004,027 A | 6/1935 | Baxter .......................... 215/74 |
| 2,009,400 A | 7/1935 | Hapgood .................... 226/116 |
| 2,073,746 A | 3/1937 | Keller ........................... 15/14 |
| 2,208,028 A | 7/1940 | Harrington .................. 226/125 |
| 2,438,769 A | 3/1948 | Thomas |
| 2,641,270 A | 6/1953 | Allen |
| 2,799,301 A | 7/1957 | Ballard ........................ 141/317 |
| 2,886,071 A | 5/1959 | Rasmussen .................. 141/82 |
| 3,171,447 A | 3/1965 | Fowler et al. ................ 141/95 |
| 3,394,831 A | 7/1968 | Bathish et al. ................ 215/42 |
| 3,482,583 A | 12/1969 | Fenn |
| 3,603,328 A | 9/1971 | Fenn |

(List continued on next page.)

FOREIGN PATENT DOCUMENTS

EP  0596132 A1  5/1994

OTHER PUBLICATIONS

Med Inc., Medical & Environmental Design, Inc.; Promotional Product Material, Jan. 15, 1991.

*Primary Examiner*—John G. Weiss
*Assistant Examiner*—Michael Bogart
(74) *Attorney, Agent, or Firm*—Michael Best & Friedrich LLP

(57) ABSTRACT

A method of removing body fluids from a patient and disposing of the body fluids, the method comprising the steps of (a) providing a container including a bottom wall having therein a drain, (b) providing a drainage device for automatically opening the drain and draining the contents of the container, (c) collecting body fluids in the container, (d) placing the container on the drainage device, and (e) operating the drainage device so that the drainage device opens the drain and drains the contents of the container.

66 Claims, 6 Drawing Sheets

U.S. PATENT DOCUMENTS

| | | | |
|---|---|---|---|
| 3,646,935 A | 3/1972 | Holbrook et al. ............ 128/276 |
| 3,671,982 A | 6/1972 | Sayles |
| 3,780,757 A | 12/1973 | Jordan |
| 3,782,414 A | 1/1974 | Holbrook .................... 135/575 |
| 3,791,394 A | 2/1974 | Hammelmann |
| 3,863,664 A | 2/1975 | Holbrook et al. ............ 137/205 |
| 3,897,599 A | 8/1975 | Artzer |
| 3,916,924 A | 11/1975 | McGowan .................... 134/95 |
| 3,945,392 A | 3/1976 | Deaton et al. .............. 137/205 |
| 3,958,730 A | 5/1976 | Caldwell |
| 3,995,333 A | 12/1976 | Stephens |
| 4,004,590 A | 1/1977 | Muriot ...................... 128/276 |
| 4,049,555 A | 9/1977 | Matherne ................... 210/409 |
| 4,053,284 A | 10/1977 | Posch ......................... 23/259 |
| 4,058,412 A | 11/1977 | Knapp et al. |
| 4,084,723 A | 4/1978 | Parker |
| 4,090,635 A | 5/1978 | Nelson et al. |
| 4,108,336 A | 8/1978 | Anderson, Jr. |
| 4,135,515 A | 1/1979 | Muriot ...................... 128/276 |
| 4,157,718 A | 6/1979 | Baehr ........................ 128/276 |
| 4,195,633 A | 4/1980 | Nehring et al. ............. 128/276 |
| 4,195,672 A | 4/1980 | Freeman |
| 4,228,798 A | 10/1980 | Deaton ...................... 128/276 |
| 4,238,892 A | 12/1980 | Geiss ........................... 34/85 |
| 4,245,637 A | 1/1981 | Nichols ...................... 128/276 |
| 4,341,568 A | 7/1982 | Christensen ................ 134/21 |
| 4,345,342 A | 8/1982 | Saito ............................ 4/301 |
| 4,356,084 A | 10/1982 | Hatton et al. |
| 4,363,340 A | 12/1982 | Naftulin ..................... 141/51 |
| 4,388,922 A | 6/1983 | Telang ....................... 604/319 |
| 4,429,803 A | 2/1984 | Butterfield ................. 215/366 |
| 4,430,084 A | 2/1984 | Deaton |
| 4,497,351 A | * 2/1985 | Garcia ....................... 141/329 |
| 4,519,427 A | 5/1985 | Ono et al. .................... 141/65 |
| 4,559,664 A | 12/1985 | Bohme et al. ................ 15/302 |
| 4,586,549 A | 5/1986 | White ........................ 141/67 |
| 4,631,050 A | 12/1986 | Reed et al. .................... 604/4 |
| 4,666,063 A | 5/1987 | Holoubek et al. .......... 222/107 |
| 4,673,006 A | 6/1987 | Speck ........................... 141/1 |
| 4,676,281 A | 6/1987 | Nord ............................ 141/1 |
| 4,676,287 A | 6/1987 | Fitzwater ................... 141/285 |
| 4,685,480 A | 8/1987 | Eck ........................... 134/182 |
| 4,735,610 A | 4/1988 | Akkas et al. ................ 604/119 |
| 4,749,010 A | 6/1988 | Petell ......................... 141/59 |
| 4,762,241 A | 8/1988 | Lang |
| 4,770,787 A | 9/1988 | Heath et al. ................. 210/646 |
| 4,795,428 A | 1/1989 | Hwang ........................ 604/73 |
| 4,808,159 A | 2/1989 | Wilson et al. ................. 604/4 |
| 4,813,563 A | 3/1989 | Ogden et al. |
| 4,820,351 A | 4/1989 | Hambleton et al. ........... 134/21 |
| 4,857,063 A | 8/1989 | Glenn ........................ 604/317 |
| 4,863,446 A | 9/1989 | Parker ....................... 604/317 |
| 4,867,738 A | 9/1989 | Mintz ............................ 604/4 |
| 4,905,325 A | 3/1990 | Colditz |
| 4,913,179 A | 4/1990 | Engel et al. ................. 134/113 |
| 4,913,197 A | 4/1990 | Friedrich ....................... 141/3 |
| 4,957,491 A | 9/1990 | Parker |
| 4,961,440 A | 10/1990 | Wright |
| 4,967,814 A | 11/1990 | Day, Jr. ..................... 141/286 |
| 4,969,491 A | 11/1990 | Kiplinger ...................... 141/1 |
| 4,972,976 A | 11/1990 | Romero |
| 5,024,613 A | 6/1991 | Vasconcellos et al. .......... 604/4 |
| 5,033,492 A | 7/1991 | Mertens et al. ......... 134/166 R |
| 5,045,077 A | 9/1991 | Blake, III ................... 604/321 |
| 5,049,273 A | 9/1991 | Knox ......................... 210/406 |
| 5,053,026 A | 10/1991 | Andersen et al. ........... 604/319 |
| 5,064,101 A | 11/1991 | Richter et al. |
| 5,067,950 A | 11/1991 | Broadnax, Jr. .............. 604/317 |
| 5,071,035 A | 12/1991 | Kiplinger ................... 222/83.5 |
| 5,119,830 A | 6/1992 | Davis ........................ 128/771 |
| 5,185,007 A | 2/1993 | Middaugh et al. .......... 604/320 |
| 5,186,195 A | 2/1993 | Wall |
| 5,192,439 A | 3/1993 | Roth et al. .................. 210/485 |
| 5,222,530 A | 6/1993 | Baker et al. |
| 5,273,083 A | 12/1993 | Burrows ...................... 141/18 |
| 5,349,995 A | 9/1994 | Perez ......................... 141/98 |
| 5,351,859 A | 10/1994 | Jansen ......................... 222/82 |
| 5,380,314 A | 1/1995 | Herweck et al. ............ 604/403 |
| 5,460,193 A | 10/1995 | Lavallois et al. |
| 5,470,324 A | 11/1995 | Cook et al. ................. 604/319 |
| 5,546,979 A | 8/1996 | Clark, II et al. ............ 137/318 |
| 5,624,417 A | 4/1997 | Cook et al. ................. 604/319 |
| 5,637,103 A | 6/1997 | Kerwin et al. .............. 604/317 |
| 5,725,516 A | 3/1998 | Cook et al. ................. 604/319 |
| 5,776,260 A | 7/1998 | Dunn et al. ................... 134/18 |
| 5,807,359 A | 9/1998 | Bemis et al. ............... 604/322 |
| 5,837,103 A | 11/1998 | Trokhan et al. |
| 5,871,476 A | 2/1999 | Hand ......................... 604/317 |
| 5,901,717 A | 5/1999 | Dunn et al. ................... 134/56 |
| 5,931,822 A | 8/1999 | Bemis et al. ............... 604/322 |

* cited by examiner

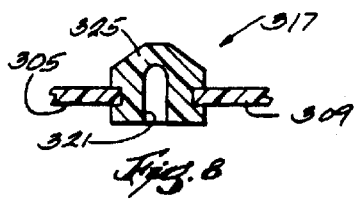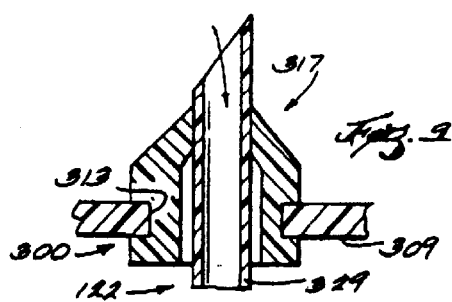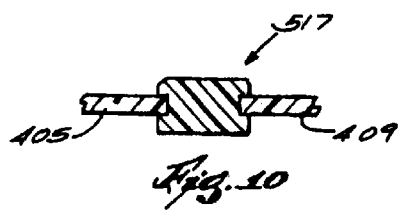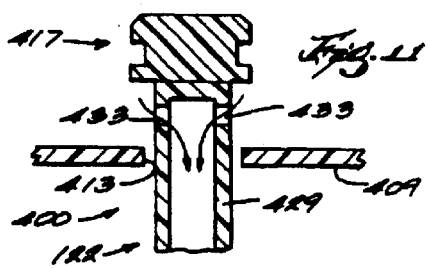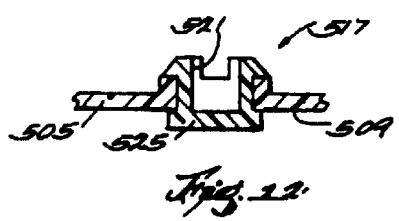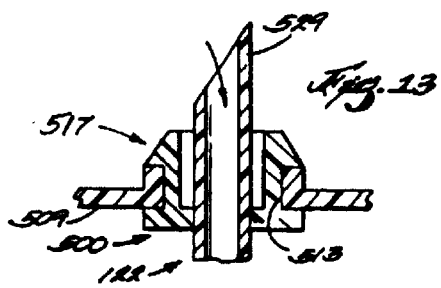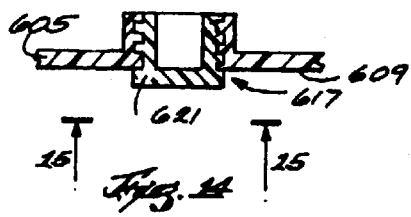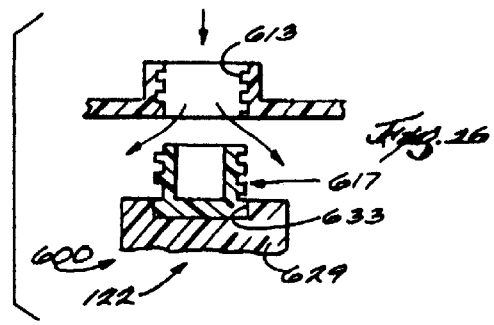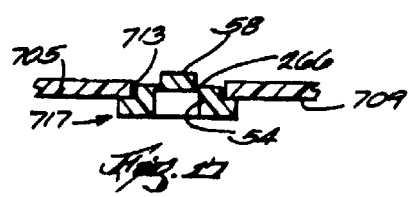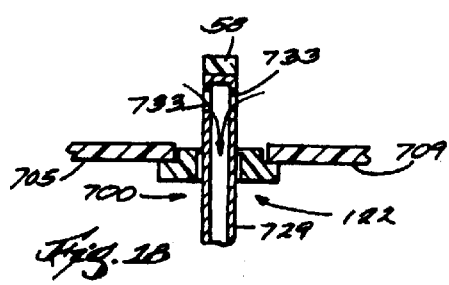

METHOD AND APPARATUS FOR REMOVING AND DISPOSING OF BODY FLUIDS

RELATED APPLICATIONS

This is a continuation-in-part of U.S. Ser. No. 08/877,771 filed Jun. 17, 1997 now U.S. Pat. No. 5,871,476, which is a divisional of U.S. Ser. No. 08/582,358 filed Jan. 5, 1996 now U.S. Pat. No. 5,688,255, which is a continuation-in-part of U.S. Ser. No. 08/547,759 filed Oct. 24, 1995 U.S. Pat. No. 5,683,371, which is a continuation-in-part of U.S. Ser. No. 08/365,695 filed Dec. 29, 1994 now U.S. Pat. No. 5,620,428.

FIELD OF THE INVENTION

The invention relates to medical methods and apparatus for removing body fluids from patients and relates to disposing of the body fluids.

BACKGROUND OF THE INVENTION

Suction canisters are used in hospital environments and particularly during various surgical procedures to store drained bodily fluid from a patient. In general, suction canisters are used in conjunction with a vacuum source which enables bodily fluid to be drained from the patient and stored in the canister. Each canister generally includes a receptacle for holding the bodily fluid, a lid with a vacuum port and a patient port, a suction conduit connecting the vacuum port to a vacuum source, and a patient conduit for conveying the bodily fluid from the patient into the receptacle through the patient port. When the suction conduit is connected to the vacuum source, a negative pressure gradient is created in the interior of the receptacle so that the bodily fluid is drawn from the patient and into the suction canister via the patient conduit.

Other types of containers, such as urine collectors and chest drainage devices, can also be used to collect body fluids.

It has become important in environments such as hospitals to eliminate the handling of and thus reduce employee exposure to bodily fluids. Currently, hospitals dispose of such bodily fluid in various ways. Bodily fluid can be poured from the suction canister down the hospital sink and into the sewer system, can be incinerated as a liquid or solid, or can be disposed of at an approved hazardous waste site. If hospital employees have to handle the bodily fluid, spattering of the bodily fluid can result in hospital employees contacting the hazardous fluid.

SUMMARY OF THE INVENTION

The invention provides improved methods and apparatus for removing body fluids from patients and relates to disposing of the body fluids.

More particularly, the invention provides a suction canister including a container having a chamber for collecting fluids, a patient port, and a vacuum port. The patient and vacuum ports communicate with the chamber. When a vacuum is created in the chamber via the vacuum port, fluid is thereby drawn into the container via the patient port. The chamber is partially defined by a wall, preferably the bottom wall, including a protrusion extending into the chamber. The protrusion defines a passageway having an open outer end and a closed inner end. The protrusion includes a thin portion such that the protrusion can be broken to provide communication between the passageway and the chamber for draining fluid contained in the suction canister.

Preferably, the passageway has an axis, the wall is molded with mold parts movable relative to each other in a direction parallel to the axis, and the thin portion has a reduced thickness in a direction parallel to the axis. This makes it easier to control the thickness of the thin portion during molding, because it is easier to control the relative positions of the mold parts in the direction of parting than in other directions. The invention preferably also provides a drainage device for breaking the thin portion of the protrusion and draining the canister.

The invention also provides a method of removing body fluids from a patient and disposing of the body fluids. The method includes the steps of providing a molded suction canister including a molded-in drain, providing a drainage device for automatically opening the molded-in drain and draining the contents of the suction canister, collecting body fluids in the suction canister, connecting the suction canister to the drainage device, and operating the drainage device so that the drainage device opens the drain and drains the contents of the suction canister.

The invention also provides another method of removing body fluids from a patient and disposing of the body fluids, the method comprising the steps of providing a container including a bottom wall having therein a drain, providing a drainage device for automatically opening the drain and draining the contents of the container, collecting body fluids in the container, placing the container on the drainage device, and operating the drainage device so that the drainage device opens the drain and drains the contents of the container. The drain can either be integrally molded with the container or provided by a plug closing an opening in the container.

The invention provides a suction canister or container that is easily drained of potentially hazardous fluid without contact with the fluid. The suction canister when used in conjunction with the drainage device allows a convenient means of disposing of the fluid content.

Other features and advantages of the invention will become apparent to those of ordinary skill in the art upon review of the following description, claims and drawings.

BRIEF DESCRIPTION OF THE DRAWINGS

FIG. 8 is a partial sectional view of the drain of a container that is a second alternative embodiment of the invention;

FIG. 9 is a view similar to FIG. 8 showing the drain being opened;

FIG. 10 is a partial sectional view of the drain of a container that is a third alternative embodiment of the invention;

FIG. 11 is a view similar to FIG. 10 showing the drain being opened;

FIG. 12 is a partial sectional view of the drain of a container that is a fourth alternative embodiment of the invention;

FIG. 13 is a view similar to FIG. 12 showing the drain being opened;

FIG. 14 is a partial sectional view of the drain of a container that is a fifth alternative embodiment of the invention;

FIG. 15 is a view taken along line 15—15 in FIG. 14;

FIG. 16 is a view similar to FIG. 14 showing the drain being opened;

FIG. 17 is a partial sectional view of the drain of a container that is a sixth alternative embodiment of the invention;

FIG. 18 is a view similar to FIG. 17 showing the drain being opened;

Figure 1:
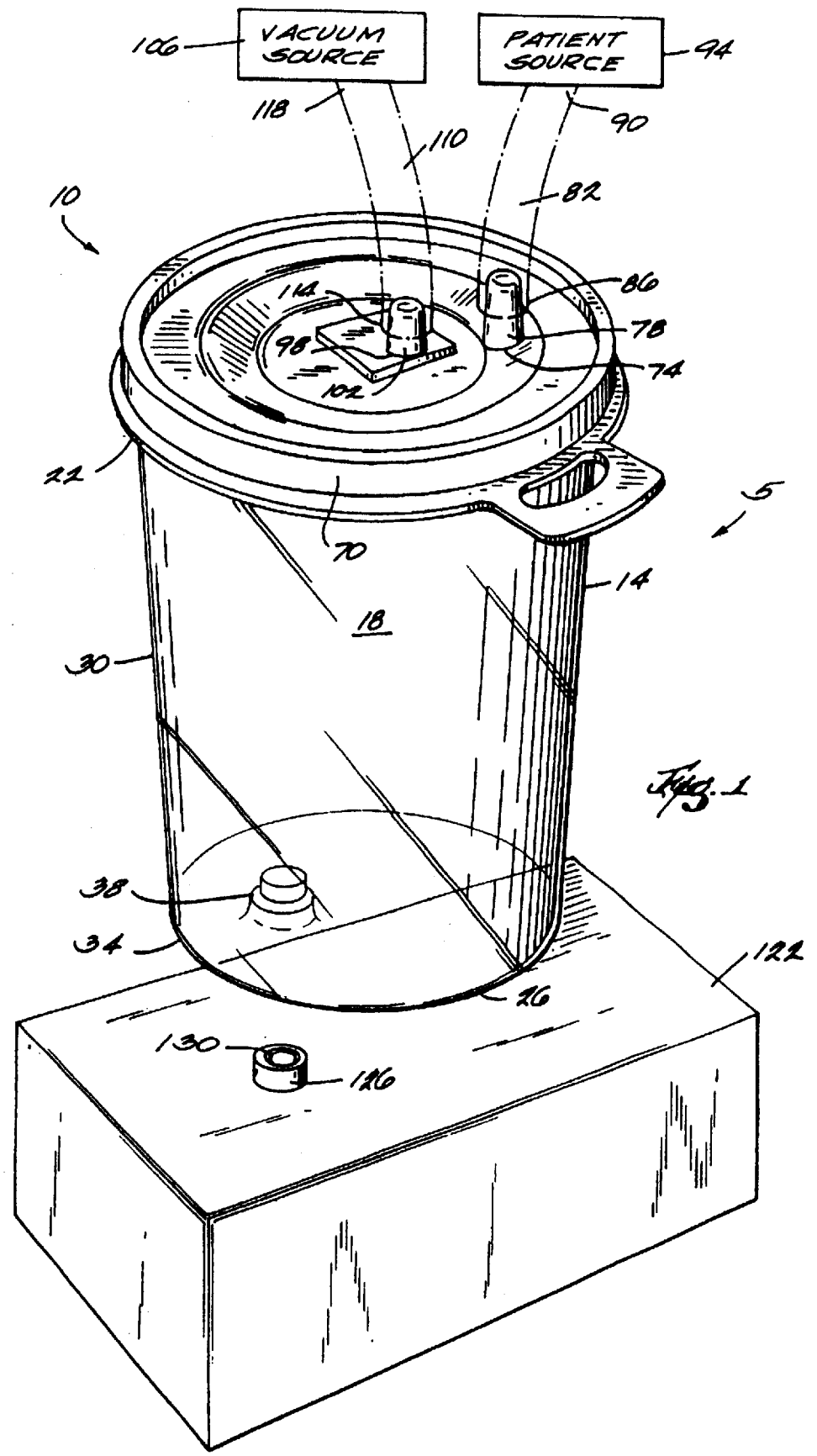
FIG. 1 is perspective view of an apparatus embodying the invention.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

Referring now to the drawings in which like reference numerals refer to like parts throughout the views, there is shown in FIGS. 1 through 5 an apparatus 5 embodying the invention. The apparatus comprises a suction canister 10. The suction canister includes a container 14 which defines a chamber 18 for collecting drained fluid. The container 14 is preferably plastic (such as clear polystyrene) and is injection molded. The container 18 has an open upper end 22 and a closed lower end 26. The container 18 is defined by an annular side wall 30 and by a bottom wall 34. The bottom wall 34 includes a molded-in drain formed by a protrusion 38 extending into the chamber 18. By "molded-in" it is meant that the container 14 and the drain are formed in a single injection molding process.

Figure 2:
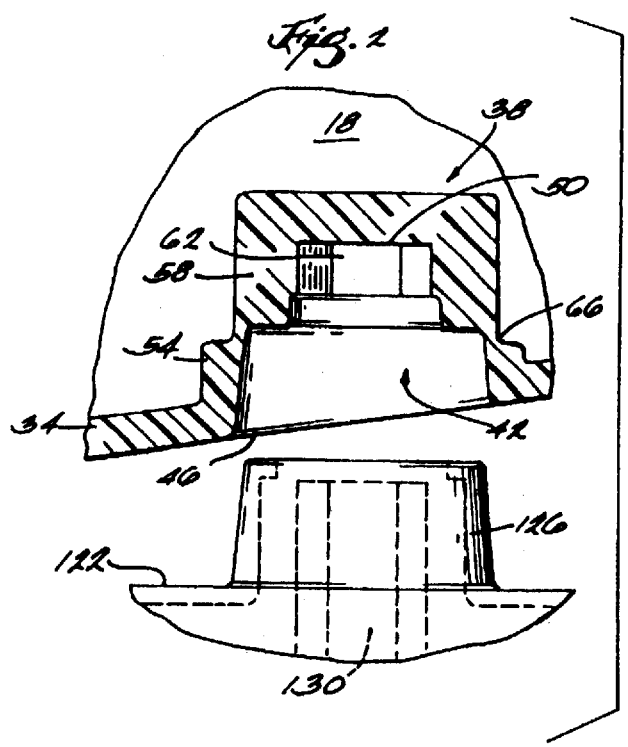
FIG. 2 is a partial sectional view of the suction canister and the drainage device.

As best shown in FIG. 2, the protrusion 38 defines a passageway 42 that tapers upwardly and has an open lower or outer end 46 and a blind or closed upper or inner end 50. More particularly, the protrusion 38 includes a first wall portion 54. The first wall portion 54 defines the outer end 46 of the passageway 42. As shown in FIG. 2, the first wall portion 54 is not uniform in height throughout its entire circumference due to a curvature of the bottom wall 34. However, it should be noted that the first wall portion 54 can be uniform in height throughout its circumference. Further, the height of the first wall portion 54 is preferably minimized to minimize the volume of fluid that remains in the suction canister 10 after it has been drained.

Figure 4:
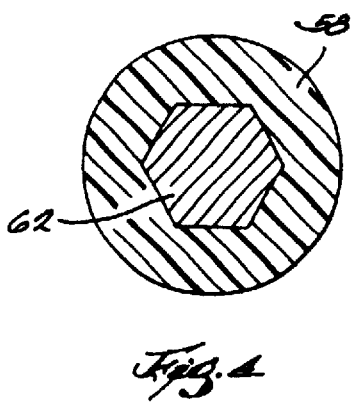
FIG. 4 is a view taken along line 4—4 of FIG. 3.

The protrusion 38 also includes a second wall portion 58 that defines the closed inner end 50 of the passageway 42. The second wall portion 58 defines an outwardly or downwardly opening, non-circular socket 62 at the inner end 50 of the passageway 42 as best shown in FIGS. 2 and 4. The socket is preferably hexagonal.

Referring now to FIG. 2, a thin or frangible wall portion 66 integrally connects the first wall portion 54 and the second wall portion 58. As will be explained in more detail hereafter, the frangible wall portion 66 can be broken to provide communication between the passageway 42 and the chamber 18 to enable draining of the fluid from the suction canister 10. The frangible wall portion 66 is small in size (preferably about 0.010 inch thick) to provide for ease of breakage when draining is desired yet is also strong enough to withstand the tensile and circumferential stresses when a vacuum is created in the chamber 18 when the suction canister 10 is being filled with fluid. Further, due to the placement and configuration of the frangible wall portion 66 and the socket 62, inadvertent breaking of the protrusion 38 is minimized.

As shown in FIG. 1, the suction canister 10 also includes a lid 70 which closes the upper end 22 of the container 14. The lid 70 has therein a patient port 74 which communicates with the chamber 18. Extending upwardly from the patient port is a patient port wall 78. To enable communication between the fluid to be drained and the patient port 74, a patient conduit 82 is affixed to the patient port wall 78 by forcing one end 86 of the patient conduit 82 over the patient port wall 78. The other end 90 of the patient conduit 82 communicates with the fluid to be drained such as in a patient cavity 94. When the patient conduit 82 is not attached to the patient port wall 78, a cap (not shown) can be placed over the patient port wall 78 to prevent any fluid from leaking from the suction canister 10.

The lid 70 of the suction canister 10 also includes a vacuum port 98 which communicates with the chamber 18 via a filter (not shown). The filter can be, for example, a hydrophobic filter. Extending upwardly from the vacuum port 98 is a vacuum port wall 102. To enable a vacuum to be created in the chamber 18 of the suction canister 10, the vacuum port 98 communicates with a vacuum source 106 via a suction conduit 110. The suction conduit 110 is affixed to the vacuum port wall 102 by forcing one end 114 of the suction conduit 110 over the vacuum port wall 102. The other end 118 of the suction conduit 110 is placed in communication with the vacuum source 106. The filter prevents contamination of the vacuum source 106. When the suction conduit 110 is not attached to the vacuum port wall 102, a cap (not shown) can be placed over the vacuum port wall 102 to prevent any fluid from leaking from the suction canister 10.

The suction canister 10 is used in the collection of fluids as follows. One end 114 of the suction conduit 110 is affixed to the vacuum port wall 102 as previously described and the other end 118 is placed in communication with the vacuum source 106. One end 86 of the patient conduit 82 is affixed to the patient port wall 78 as previously described and the other end 90 is placed in communication with the fluid to be drained such as in the patient cavity 94. When the vacuum source 106 is on, a vacuum is created in the chamber 18 of the container 14 such that fluid is drawn from the patient cavity 94, through the patient conduit 82 and into the container 14 via the patient port 74.

When the container 14 is filled with fluid or fluid no longer needs to be collected, the patient conduit 82 and the suction conduit 110 can be detached from the lid 70 of the suction canister 10. The caps can then be placed on the patient port wall 78 and the vacuum port wall 114 as previously described to prevent fluid from leaking from the container 14. The suction canister 10 can then be stored until the suction canister is to be drained of its fluid contents.

The apparatus 5 also comprises a drainage device 122 with an upwardly tapered drain conduit 126 and a movable tool 130 as shown in FIG. 1. Preferably, the drainage device 122 uses water pressure and a venturi to create a vacuum that suctions the fluid from the container 14 and delivers this fluid directly to the sanitary sewer line. The drainage device 122 can include a device such as the Deknatel EDUCTOR™ manufactured by Deknatel, Inc. of Fall River, Mass. A suitable drainage device is also disclosed in U.S. Pat. No. 5,217,038, which is incorporated herein by reference.

Figure 3:
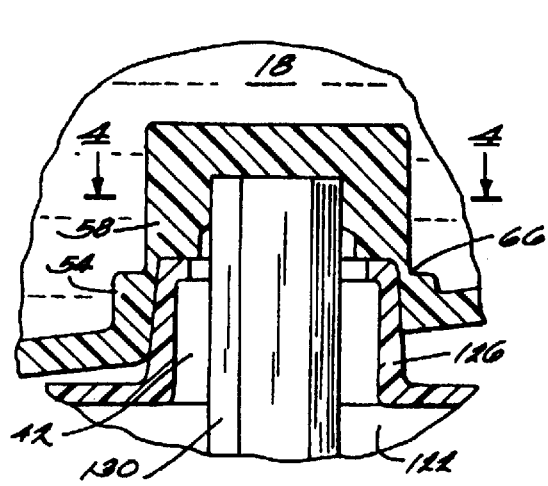
FIG. 3 is a view similar to FIG. 2 with the suction canister connected to the drainage device.
Figure 5:
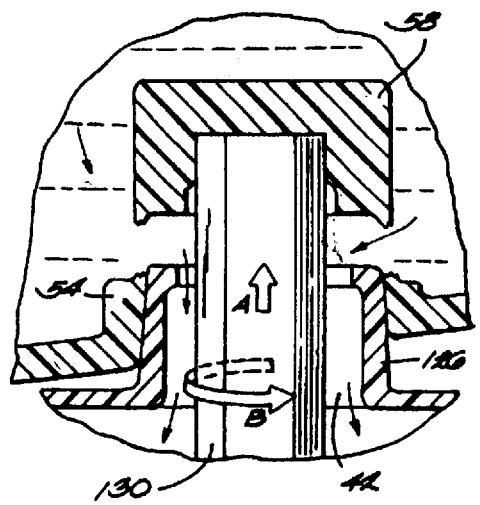
FIG. 5 is a view similar to FIG. 3 with the tool of the drainage device breaking the protrusion of the suction canister.

To enable the fluid in the container 14 to be drained, the drainage device 122 breaks the protrusion 38 as follows. When a suction canister 10 needs to be drained, the suction canister 10 is placed onto the drainage device 122 so that the drain conduit 126 of the drainage device 122 is inserted into the passageway 42 of the suction canister 10 as shown in FIG. 3. The drain conduit 126 has a configuration that is complementary to the passageway 42. A friction fit between the drain conduit 126 and the first wall portion 54 of the suction canister 10 provides a fluid seal. When the drain conduit 126 is fully wedged into the passageway 42 and the seal formed, the tool 130 is extended upwardly from the drainage device 122 and into the socket 62 of the passageway 42 as shown in FIG. 3. The tool 130 has a configuration that is complementary to that of the socket 62. Referring now to FIG. 5, further upward movement of the tool 130 (as depicted by arrow A) in conjunction with rotational movement of the tool 130 (as depicted by arrow B) breaks the frangible wall portion 66 of the protrusion 38, thereby disconnecting the second wall portion 58 from the first wall portion 54. The breakage of the protrusion 38 allows the fluid within the container 14 to exit the chamber 18 and enter the drainage device 122 via the drain conduit 126. As shown by the small arrows in FIG. 5, the fluid flows through the conduit 126 around the tool 130. The seal between the drain conduit 126 and the first wall portion 54 of the protrusion 38 prevents fluid from flowing anywhere but through the passageway 42 and into the drainage device 122.

During drainage of the fluid from the suction canister 10, the caps on the patient port wall 78 and/or the vacuum port wall 102 can be removed to vent the chamber 18 to aid in drainage of the fluid. Alternatively, a vent could be provided in the drainage device 122 to aid in drainage of the fluid from the suction canister 10.

Figure 6:
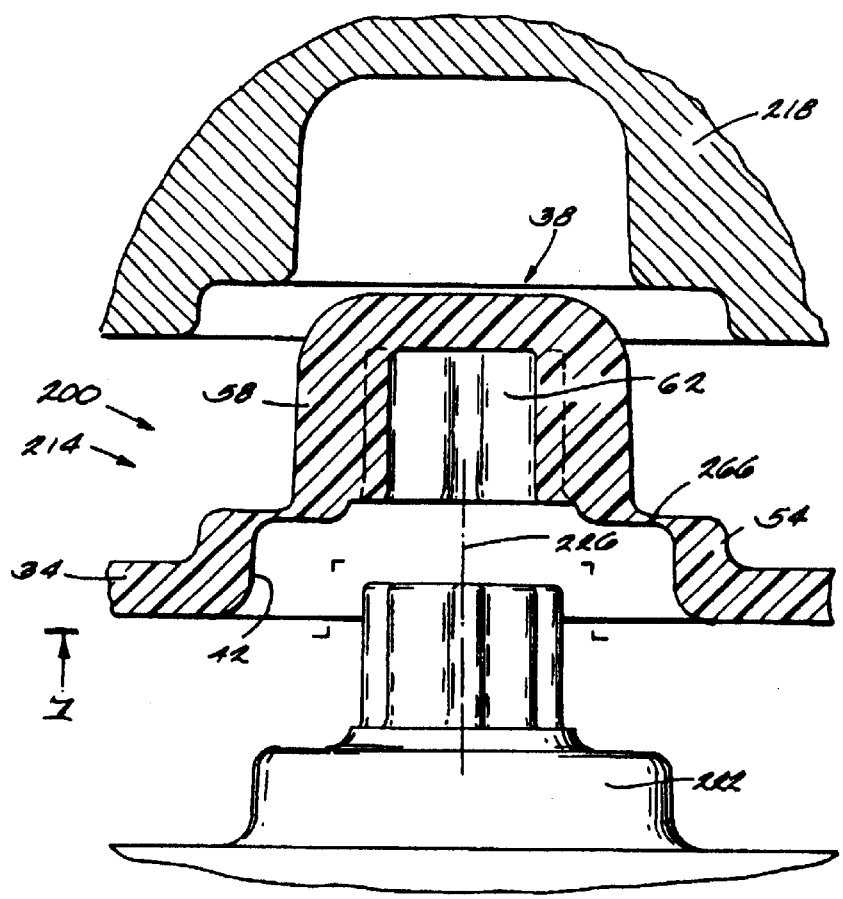
FIG. 6 is a view similar to FIG. 2 showing an alternative construction and mold parts.
Figure 7:
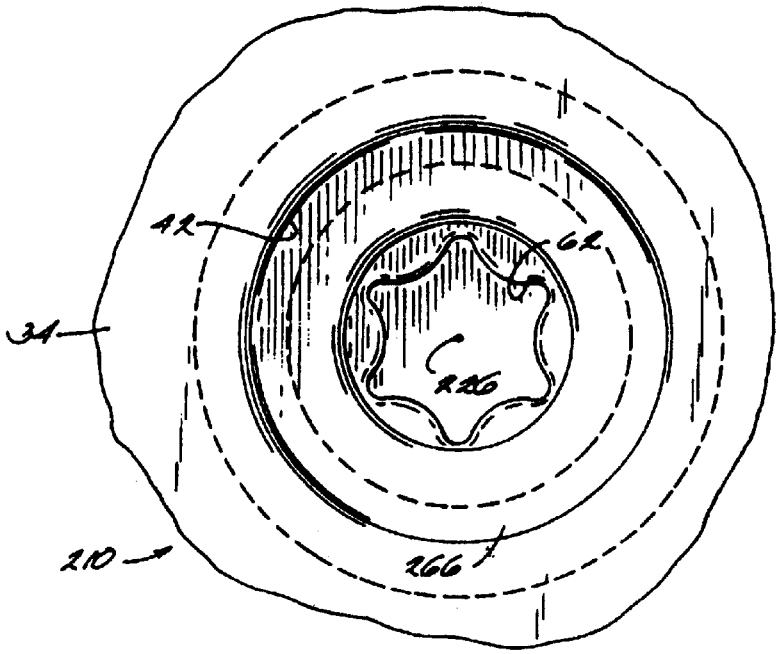
FIG. 7 is view taken along line 7—7 in FIG. 6.

An apparatus 200 which is a first alternative embodiment of the invention is illustrated in FIGS. 6 and 7. Except as described below, the apparatus 200 is identical to the apparatus 5, and common elements have been given the same reference numerals.

The apparatus 200 comprises a suction canister 210 including a container 214. The container 214 is preferably made of clear polystyrene. The passageway 42 has an axis 226, and the container 214 is preferably injection molded using mold parts 218 and 222 which are movable relative to each other or part in the direction of the axis 226. In other words, the mold parts 218 and 222 part vertically as shown in FIG. 6. This is identical to the manner in which the container 14 shown in FIGS. 1–5 is preferably molded.

It has been found that it can be difficult to control the thickness of the thin wall portion 66 of the container 14 because it can be difficult to precisely maintain the relative horizontal positions of the mold parts during molding. Any sideways or horizontal movement of one mold part relative to the other can have a significant effect on the thickness of the thin wall portion 66, because the wall portion 66 has a reduced thickness in the horizontal direction. On the other hand, it is relatively easy to maintain the relative vertical positions of the mold parts, i.e., the spacing of the mold parts in the direction of parting.

For this reason, the container 214 has a thin wall portion 266 with a reduced thickness in the direction of parting of the mold parts 218 and 222, i.e., in the vertical direction in FIG. 6. Viewed another way, the thin wall portion 266 has a reduced thickness in a direction parallel to the axis 226. The thickness of the wall portion 266 is preferably 0.010 inch, and can be relatively easily controlled. The wall portion 266 also has a radial or horizontal dimension that is substantially greater than the reduced thickness. This radial dimension is preferably approximately 0.060 inch. Variation of this dimension during molding is not critical. The thin wall portion 266 is easily broken when draining is desired yet is also strong enough to withstand the stress of a vacuum in the chamber 18. In fact, it has been found that the thin wall portion 266 can be broken simply by pushing upwardly on the second wall portion 58. It is not necessary to twist the wall portion 58 in order to break the wall portion 266.

The container 214 also differs from the container 14 in that the socket 62 is star-shaped rather than hexagonal. Obviously, any non-circular shape can be employed.

It should be noted that the bottom wall of the container could be conical or sloped toward the drain for improved drainage.

An apparatus 300 which is a second alternative embodiment of the invention is illustrated in FIGS. 8 and 9. Except as described below, the apparatus 300 is identical to the apparatus 5, and common elements have been given the same reference numerals.

The apparatus 300 comprises a container 305 with a bottom wall 309 having therein an opening 313 closed by a plug 317 inserted in the opening 313. The plug 317 is preferably made of an elastomer or thermoplastic and snaps into the opening. The plug has therein a blind central passageway 321 with a closed upper end 325. AS shown in FIG. 9, the drainage device 122 includes a pointed conduit or hollow needle 329 that pierces the upper end 325 of the passageway 321 so that fluid flows out of the container 305 through the needle or conduit 329.

An apparatus 400 which is a third alternative embodiment of the invention is illustrated in FIGS. 10 and 11. Except as described below, the apparatus 400 is identical to the apparatus 5, and common elements have been given the same reference numerals.

The apparatus 400 comprises a container 405 with a bottom wall 409 having therein an opening 413 closed by a plug 417 inserted in the opening 413. The plug 417 is preferably made of an elastomer or thermoplastic and snaps into the opening. As shown in FIG. 11, the drainage device 122 includes a conduit 429 with a closed upper end and side openings 433. The conduit 429 pushes the plug up into the container 405 so that fluid flows out of the container 405 through the openings 433 and into the conduit 429.

An apparatus 500 which is a fourth alternative embodiment of the invention is illustrated in FIGS. 12 and 13. Except as described below, the apparatus 500 is identical to the apparatus 5, and common elements have been given the same reference numerals.

The apparatus 500 comprises a container 505 with a bottom wall 509 having therein an opening 513 closed by a plug 517 inserted in the opening 513. The plug 517 is preferably made of a thermoplastic and snaps into the opening. The plug has therein a blind central passageway 521 with a closed lower end 525. As shown in FIG. 13, the drainage device 122 includes a pointed conduit or hollow needle 529 that pierces the lower end 525 of the passageway 521 so that fluid flows out of the container 505 through the needle or conduit 529.

An apparatus 600 which is a fifth alternative embodiment of the invention is illustrated in FIGS. 14–16. Except as described below, the apparatus 600 is identical to the apparatus 5, and common elements have been given the same reference numerals.

The apparatus 600 comprises a container 605 with a bottom wall 609 having therein an internally threaded opening 613 closed by a plug 617. The plug 617 is preferably made of a thermoplastic and threads into the opening 613. As shown in FIG. 15, the plug has a hexagonal head 621. As shown in FIG. 16, the drainage device 122 includes a tool 629 with a socket 633 that engages the plug head 621 and unthreads the plug 617 from the opening 613 so that fluid flows out of the container 605 through the opening 613.

An apparatus 700 which is a sixth alternative embodiment of the invention is illustrated in FIGS. 17 and 18. Except as described below, the apparatus 700 is identical to the apparatus 5, and common elements have been given the same reference numerals.

The apparatus 700 comprises a container 705 with a bottom wall 709 having therein an opening 713 closed by a plug 717. The plug 717 is preferably made of a thermoplastic and is glued, ultrasonically welded or otherwise secured over the opening. The plug 717 has a construction similar to the bottom wall of the container 214 shown in FIGS. 6 and 7. Thus, the plug 717 has a first wall portion 54, a second wall portion 58 and a frangible wall portion 266 like those of the suction canister 210. As shown in FIG. 18, the drainage device 122 includes a conduit 729 with a closed upper end and side openings 733. The conduit 729 breaks the thin wall portion 721 and extends into the container 705 so that fluid flows out of the container 705 through the openings 733 and into the conduit 729.

An apparatus which is a seventh alternative embodiment of the invention is illustrated in FIGS. 19–23. Except as described below, the apparatus is identical to the apparatus 5, and common elements have been given the same reference numerals.

Figure 19:
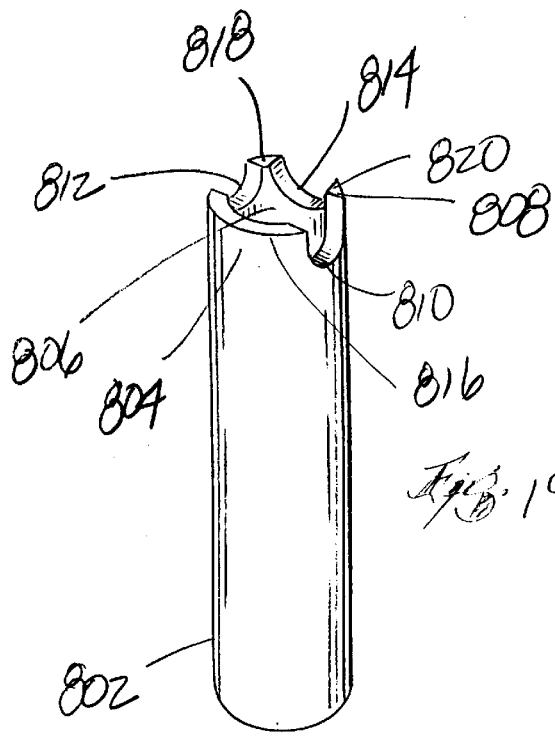
FIG. 19 is a perspective view of a drain pipe that is the seventh embodiment of the invention.
Figure 21:
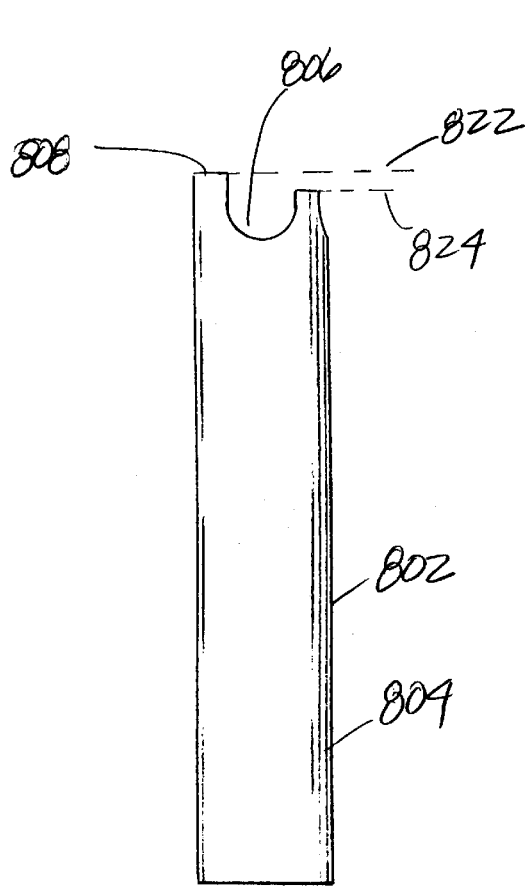
FIG. 21 is a side view of the drain pipe.
Figure 20:
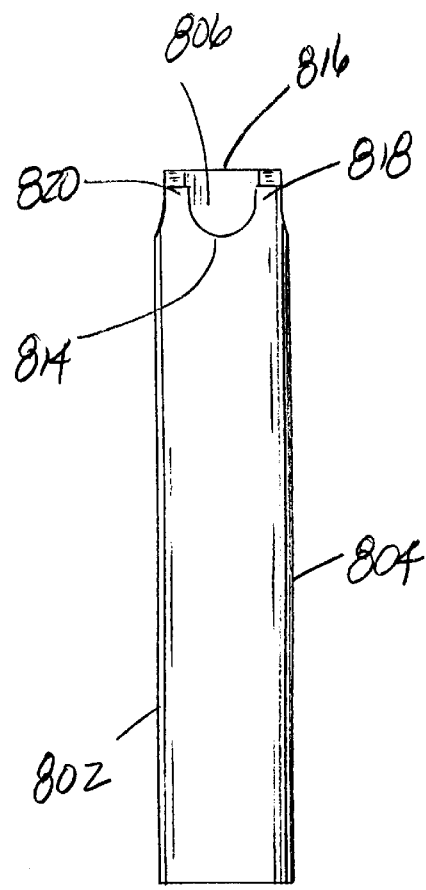
FIG. 20 is a front view of the drain pipe.

The apparatus comprises a drain pipe 802 as particularly shown in FIGS. 19–21. The drain pipe 802 includes a cylindrical wall 804 which defines a central passageway 806. The wall 804 terminates in an end surface 808 such that the passageway 806 is accessible from the end surface 808. The drain pipe 802 has therein three generally U-shaped recesses 810, 812 and 814 in the wall 804 and adjacent the end surface 808. A first portion 816 of the wall 804 is located between the recess 810 and the recess 812. A second portion 818 of the wall 804 is located between the recess 812 and the recess 814. A third portion 820 of the wall 804 is located between the recess 814 and the recess 810. Preferably, the first portion 816 includes more of the circumference of the end surface 808 of the wall 804 than do the second or third portions 818 and 820, respectively.

The first portion 816 of the wall 804 does not terminate in a common plane with the second or third portions 818 and 820, respectively. Instead, the first portion 816 terminates in a first plane 822 and the second and third portions 818 and 820, respectively terminate in a second plane 824.

Figure 22:
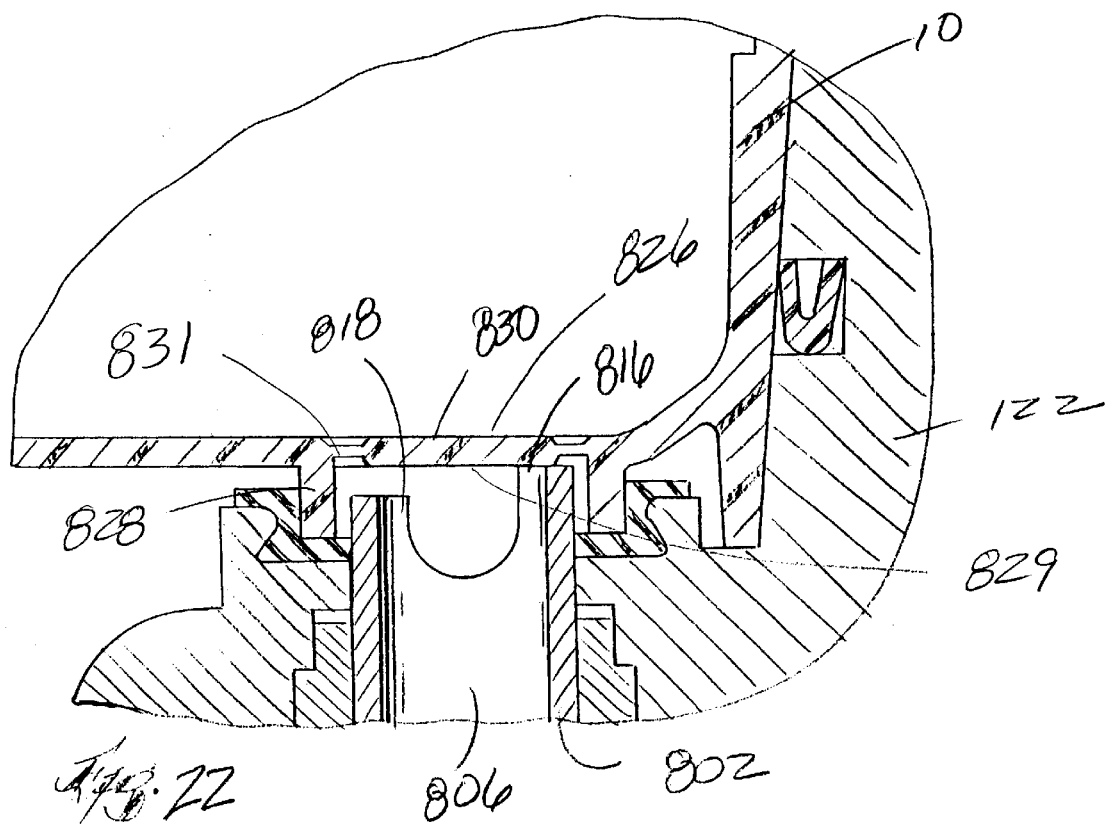
FIG. 22 is a partial sectional view of the drain pipe and the suction canister in a first or ready position.

In operation, the drain pipe 802 interacts with the suction canister 10 as follows. Referring to FIG. 22, the suction canister 10 is positioned on the drainage device 122 such that a drain 826 is positioned adjacent the drain pipe 802. The drain 826 includes a cylindrical wall 828 that defines a drain port 829 that is preferably generally circular, however, other configurations of the port 829 could also be used. A cap or cover 830 over the drain port 829. Preferably, the cap 830 is formed such that the material is thinner around the periphery 831 of the cap 830 than the remainder of the cap 830 or the wall 828.

Preferably, the wall 828 and the cap 830 are integral with the suction canister 10 so as to define a molded-in drain. However, it should be noted that the invention is not limited to the use of a molded-in drain. Further, preferably the drain port 829 is located at the bottom of the suction canister 10, however, other locations of the drain port 829 could also be used.

In a first or ready position shown in FIG. 22, the drain pipe 802 is spaced from the cap 830 and the cap 830 covers or blocks the drain port 829 to prevent fluid from exiting the suction canister 10 via the drain port 829.

To open the drain 826 so as to allow the fluid held in the suction canister 10 to drain out of the suction canister 10, the drainage device 122 dislodges or moves the cap 830 so that fluid can flow out of the suction canister 10 via the drain port 829. In the preferred embodiment, the drainage device 122 utilizes the drain pipe 802 to dislodge the cap 830. Specifically, the drainage device 122 moves the pipe drain 802 into contact with the cap 830. In the preferred embodiment, the drainage device 122 moves the drain pipe 802 upwardly to contact the cap 830 on the bottom of the suction canister 10. It should be noted that the suction canister 10 could also be moved into contact with the drain pipe 802.

As the drain pipe 802 moves upwardly, the first portion 816 is the first part of the drain pipe 802 to contact the cap 830. Further upward movement of the drain pipe 802 begins to break or sever the connection between the wall 828 and the cap 830 at a location adjacent the first portion 816 of the pipe drain 802. Continued upward movement of the pipe drain 802 continues to break the connection between the wall 828 and the cap 830 around almost, but not all of, the periphery of the cap 830.

Because the second and third portions 818 and 820, respectively, of the drain pipe 802 terminate in the plane 824 that is spaced from the plane 822 in which the first portion 816 terminates, the connection between the cap 830 and the wall 828 around the periphery of the cap 830 is not completely severed. Instead, and with reference to FIG. 23, a hinge 832 remains intact so that the cap 830 does not completely release from the suction canister 10. As the drain pipe 802 ceases its upward movement, the second and third portions 818 and 820, respectively, of the drain pipe 802 cause the cap 830 to pivot about the hinge 832 to a generally vertical position, termed the second or draining position. The drain pipe 802 holds or fixes the cap 830 in this second position and does not allow the cap 830 to move within the interior of the suction canister 10.

Figure 23:
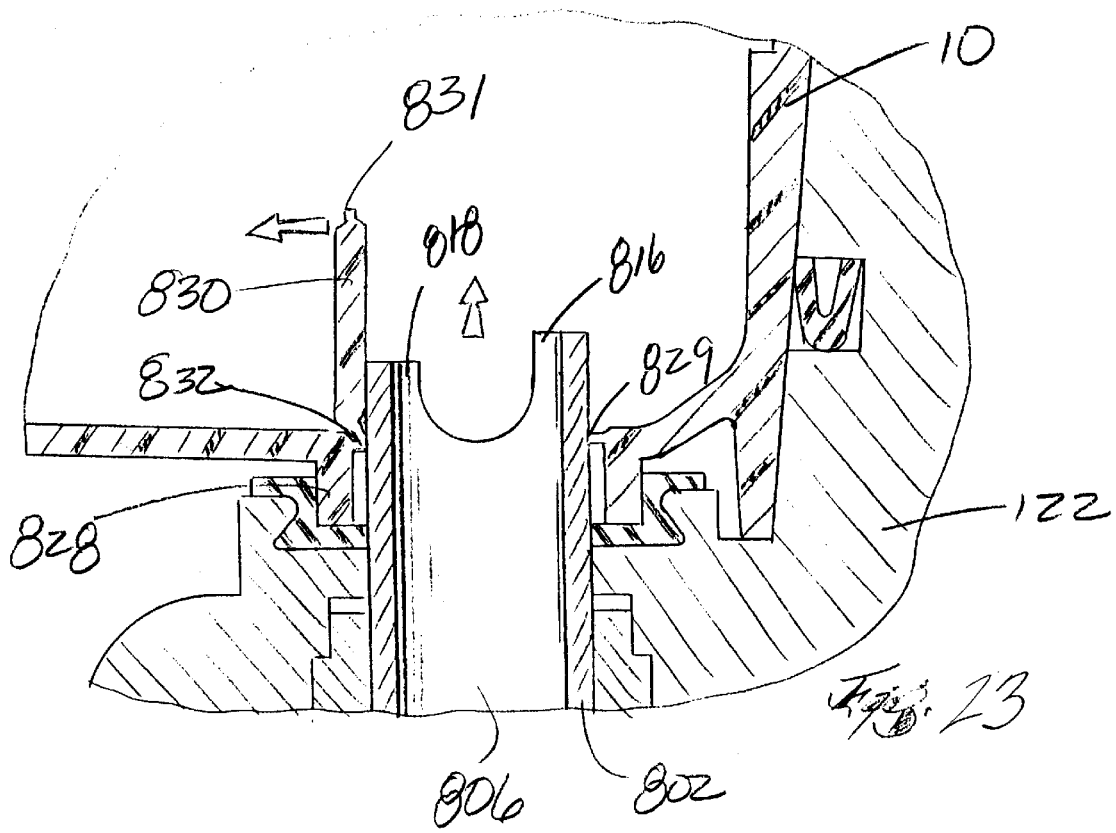
FIG. 23 is a partial section view of the drain pipe and the suction canister in a second or draining position.

With the cap 830 in its second position as in shown in FIG. 23, the fluid held in the suction canister 10 can drain through the passageway 806 in the drain pipe 802 then through the drainage device 122 to the sewer. An advantage of a cap that does not completely sever from the suction canister 10 is that the cap can be positioned and maintained in that position so as not to block the drainage of the fluid through the drain pipe 802. If the cap 830 completely severed from the suction canister 10, the combination of the fluid flow and suction can lodge the cap 830 over the drain pipe 802 and block or partially block fluid flow through the passageway 806. However, it should be noted that if desired, the drain pipe 802 could completely sever the cap 830 from the suction canister 10 by further upward movement of the drain pipe 802.

It should also be noted that, if desired and depending upon the plastic used to fabricate the suction canister 10, the portion of the connection between the wall 828 and the cap 830 that will act as the hinge 832 can be injection molded with more plastic such that the hinge 832 is thicker than the rest of the periphery of the connection between the wall 828 and the cap 830. A thicker plastic in the hinge 832 can reinforce the hinge 832 and further prevent the cap 830 from completely dislodging from the suction canister 10.

While several drain arrangements and drain opening devices have been disclosed, it should be understood that other types of drains and other devices for opening drains are within the scope of the invention.

Various features of the invention are set forth in the following claims, wherein the term "container" includes suction canisters, urine collectors, chest drainage devices and other types of containers for collecting body fluids.

We claim:

1. A medical apparatus comprising:
   a suction canister for containing fluid suctioned from a patient, said suction canister including a drain portion; and
   a drainage device including a tool actuable to dislodge said drain portion such that said drain portion remains connected to said suction canister and allows contained fluid to flow out of said suction canister.

2. The medical apparatus of claim 1 wherein said suction canister has a bottom wall, and wherein said drain portion is located in said bottom wall.

3. The medical apparatus of claim 1 wherein said tool includes a passageway and fluid flows out of said suction canister through said passageway.

4. The medical apparatus of claim 1 wherein said tool dislodges said drain portion such that said drain portion remains hingeably connected to said suction canister.

5. The medical apparatus of claim 4 wherein said suction canister has an interior, and wherein said drain portion remains hingeably connected to said suction canister in said interior of said suction canister.

6. The medical apparatus of claim 1 wherein said tool is actuable to dislodge said drain portion to a position that is generally perpendicular to the position of said drain device before it was dislodged.

7. The medical apparatus of claim 1 wherein said tool is actuable to dislodge and hold said drain portion in a fixed position.

8. The medical apparatus of claim 1 wherein said tool includes a wall having a first portion that terminates in a first plane and having a second portion that terminates in a second plane.

9. The medical apparatus of claim 1 wherein said tool terminates in an end surface, and wherein said end surface includes at least two portions that do not terminate in the same plane.

10. A medical apparatus comprising:
    a suction canister for containing fluid suctioned from a patient, said suction canister including a drainage port and a cap covering said drainage port when said cap is in a first position; and
    a drainage device including a tool actuable to move said cap from said first position to a second position that is fixed relative to said tool and to allow contained fluid to flow out of said port without interference from said cap.

11. The medical apparatus of claim 10 wherein said cap in its first position is integral with said suction canister.

12. The medical apparatus of claim 10 wherein said tool is actuable to move said cap such that in said second position, said cap remains in contact with said suction canister.

13. The medical apparatus of claim 10 wherein said tool is actuable to pivotally move said cap about a hinge such that in said second position, said cap is hingeably connected to said suction canister.

14. The medical apparatus of claim 10 wherein said tool is actuable to pivotally move said cap from said first position to said second position.

15. The medical apparatus of claim 14 wherein said cap pivots from a generally horizontal position to a generally vertical position.

16. The medical apparatus of claim 10 wherein said suction canister has a bottom wall, and wherein said drainage port is located in said bottom wall.

17. The medical apparatus of claim 10 wherein said tool terminates in an end surface, and wherein said end surface includes at least two portions that terminate in differing planes.

18. The medical apparatus of claim 10 wherein said tool includes a passageway and fluid flows out of said port through said passageway.

19. The medical apparatus of claim 10 wherein said tool moves upwardly to move said cap from said first position to said second position.

20. A medical apparatus comprising:
    a suction canister for containing fluid suctioned from a patient, said suction canister including a drain port and a cap covering said port; and
    a drainage device including a tool actuable to partially sever said cap from said suction canister such that contained fluid is able to flow out of said suction canister through said port.

21. The medical apparatus of claim 20 wherein said tool includes a passageway, and wherein the contained fluid flows out of said suction canister through said passageway.

22. The medical apparatus of claim 20 wherein said cap is integral with said suction canister.

23. The medical apparatus of claim 20 wherein said suction canister has an interior, and wherein when said cap is partially severed, said cap is moved into said interior of said suction canister.

24. The medical apparatus of claim 23 wherein said cap is moved from a generally horizontal position to a generally vertical position.

25. The medical apparatus of claim 20 wherein said tool holds said severed cap in a fixed position relative to said suction canister.

26. The medical apparatus of claim 20 wherein said tool includes a wall that contacts said cap, said wall having a first portion that terminates in a first plane and having a second portion that terminates in a second plane.

27. The medical apparatus of claim 20 wherein said tool terminates in an end surface, and wherein said end surface includes at least two portions that terminate in spaced apart planes.

28. The medical apparatus of claim 20 wherein said tool is actuated upwardly.

29. The medical apparatus of claim 20 wherein said suction canister has a bottom, and wherein said port is located in said bottom.

30. A medical apparatus comprising:
a suction canister for containing fluid suctioned from a patient, said suction canister including a drainage port and a cap covering said drainage port when said cap is in a first position; and
a drainage device including a tool actuable to move said cap from said first position to a second position to allow contained fluid to flow out of said port.

31. The medical apparatus of claim 30 wherein said suction canister has a bottom, and wherein said port is in said bottom.

32. The medical apparatus of claim 30 wherein said tool includes a fluid passageway, and wherein when said cap is in said second position, the contained fluid flows out of said port through said passageway.

33. The medical apparatus of claim 30 wherein said tool is actuated upwardly to move said cap from said first position to said second position.

34. The medical apparatus of claim 30 wherein said suction canister has an interior, and wherein when said cap is in said second position, said cap is located in said interior.

35. The medical apparatus of claim 30 wherein said cap is integral with said suction canister.

36. A medical apparatus comprising:
a suction canister including a chamber for containing fluid suctioned from a patient, said canister including a drain port and a cover positioned to prevent communication between said chamber and said drain port; and
a drainage device including a tool actuable to move said cover to provide communication between said chamber and said drain port to thereby drain contained fluid from said suction canister.

37. The medical apparatus of claim 36 wherein said suction canister includes a bottom wall, and wherein said drain port is in said bottom wall.

38. The medical apparatus of claim 36 wherein said tool includes a fluid passageway, and wherein the contained fluid flows out of said port through said passageway.

39. The medical apparatus of claim 36 wherein said tool is actuated upwardly to move said cover.

40. The medical apparatus of claim 36 wherein said cover is moved into said chamber.

41. The medical apparatus of claim 36 wherein said cover is integral with said suction canister.

42. A medical suction system comprising:
a suction canister including a bottom wall having a generally horizontal portion and including a second wall extending upwardly from said bottom wall, said bottom wall and said second wall defining a single interior cavity for holding bodily fluids, said portion of said bottom wall having therein a selectively openable drain; and
a drainage device having a suction canister support area on which said canister is positionable, said canister being supported on said support area by said bottom wall, and including a tool adapted to open said drain so as to allow bodily fluids to exit from said cavity through said drain and into said device.

43. The medical suction system of claim 42 wherein said drain is a molded-in drain.

44. The medical suction system of claim 42 wherein said tool directly engages said drain.

45. The medical suction system of claim 42 wherein said suction canister includes an open upper end, and further including a lid closing said upper end and having therein a patient port and a suction port.

46. The medical suction system of claim 42 wherein said tool is insertable into said cavity through said drain.

47. A medical suction system comprising:
a suction canister including a bottom wall having a generally horizontal portion and a second wall extending upwardly from said bottom wall, said bottom wall and said second wall defining a single interior cavity for holding bodily fluids, said portion of said bottom wall having therein a drain member having a first position wherein bodily fluids are held in said cavity and having a second position wherein bodily fluids are allowed to exit said cavity; and
a drainage device having a suction canister support area onto which said canister is positionable and a tool insertable into said cavity to cause said drain member to be moved from said first position to said second position such that the bodily fluids exit said canister into said device.

48. The medical suction system of claim 47 wherein said drain member is molded into said bottom wall.

49. The medical suction system of claim 47 wherein said tool is a probe.

50. The medical suction system of claim 47 wherein said tool enters said cavity through said bottom wall.

51. The medical suction system of claim 47 wherein said tool directly engages said drain member to move said drain member from said first position to said second position.

52. The medical suction system of claim 47 wherein said suction canister includes an open upper end, and further including a lid closing said upper end and having therein a patient port and a suction port.

53. A medical suction system comprising:
a suction canister including a bottom wall having a generally horizontal portion and a second wall extending upwardly from said bottom wall, said bottom wall and said second wall defining a single interior cavity for holding bodily fluids, said portion of said bottom wall having therein a drain; and
a drainage device having a suction canister support area on which said canister is positionable and having a tool insertable into said cavity to thereby open said drain causing bodily fluids to exit said canister into said device.

54. The medical suction system of claim 53 wherein said drain includes a molded-in drain.

55. The medical suction system of claim 53 wherein said tool enters said cavity through said bottom wall.

56. The medical suction system of claim 53 wherein said tool directly engages said drain.

57. The medical suction system of claim 53 wherein said suction canister includes an open upper end, and further including a lid closing said upper end and having therein a patient port and a suction port.

58. A medical apparatus comprising:
a suction canister for containing fluid suctioned from a patient;
a drain in said suction canister;
a drain portion covering said drain; and
a tool actuable to dislodge said drain portion such that said drain portion remains connected to said suction canister and allows contained fluid to flow out of said suction canister.

59. The medical apparatus of claim 58 wherein said suction canister has a bottom wall, and wherein said drain and said drain portion are located in said bottom wall.

60. The medical apparatus of claim 58 wherein said tool includes a passageway and fluid flows out of said suction canister through said passageway.

61. The medical apparatus of claim 58 wherein said tool dislodges said drain portion such that said drain portion remains hingeably connected to said suction canister.

62. The medical apparatus of claim 61 wherein said suction canister has an interior, and wherein said drain portion remains hingeably connected to said suction canister in said interior of said suction canister.

63. The medical apparatus of claim 58 wherein said tool is actuable to dislodge said drain portion to a position that is generally perpendicular to the position of said drain device before it was dislodged.

64. The medical apparatus of claim 58 wherein said tool is actuable to dislodge and hold said drain portion in a fixed position.

65. The medical apparatus of claim 58 wherein said tool includes a wall having a first portion that terminates in a first plane and having a second portion that terminates in a second plane.

66. The medical apparatus of claim 50 wherein said tool terminates in an end surface, and wherein said end surface includes at least two portions that do not terminate in the same plane.

* * * * *